US006955540B2

United States Patent
Mayer et al.

(10) Patent No.: US 6,955,540 B2
(45) Date of Patent: Oct. 18, 2005

(54) PREPARATION FOR BEING FASTENED ON A NATURAL TOOTH PART OR TOOTH AND CORRESPONDING FASTENING METHOD

(75) Inventors: Jorg Mayer, Niederlenz (CH); Marcel Aeschlimann, Ligerz (CH); Laurent Torriani, Biel (CH)

(73) Assignee: Woodwelding AG, Zurich (CH)

( * ) Notice: Subject to any disclaimer, the term of this patent is extended or adjusted under 35 U.S.C. 154(b) by 215 days.

(21) Appl. No.: 10/417,909

(22) Filed: Apr. 17, 2003

(65) Prior Publication Data

US 2004/0038178 A1 Feb. 26, 2004

(30) Foreign Application Priority Data

Aug. 23, 2002 (CH) ............................................... 1460/02

(51) Int. Cl.$^7$ .............................................. A61C 13/28
(52) U.S. Cl. ...................................... 433/169; 433/172
(58) Field of Search ................................ 433/172, 173, 433/174, 175, 176, 169

(56) References Cited

U.S. PATENT DOCUMENTS

| | | |
|---|---|---|
| 772,029 A | 10/1904 | Clark |
| 2,366,274 A | 1/1945 | Luth et al. |
| 2,458,152 A | 1/1949 | Eakins |
| 2,510,693 A | 6/1950 | Green |
| 2,942,748 A | 6/1960 | Anderson |
| 3,184,353 A | 5/1965 | Balamuth et al. |
| 3,481,803 A | 12/1969 | Hewitt |
| 3,499,222 A | 3/1970 | Linkow et al. |
| 3,723,215 A | 3/1973 | Kessler |
| 3,919,775 A | 11/1975 | Malmin |
| 4,032,803 A | 6/1977 | Durr et al. |
| 4,100,954 A | 7/1978 | Muller et al. |
| 4,130,751 A | 12/1978 | Gordon |
| 4,248,232 A | 2/1981 | Engelbrecht et al. |

(Continued)

FOREIGN PATENT DOCUMENTS

| | | |
|---|---|---|
| DE | 2418198 | 4/1974 |
| DE | 3045706 | 12/1980 |

(Continued)

OTHER PUBLICATIONS

Reader's Digest Complete Do–it–Yourself Manual (p. 69).

Primary Examiner—Cary E. O'Connor
Assistant Examiner—Candice C. Stokes
(74) Attorney, Agent, or Firm—Rankin, Hill, Porter & Clark LLP (57) ABSTRACT

A preparation (10, 11,12,13) to be fixed to a natural tooth part or tooth, in particular for the replacement of a load-bearing tooth part, is for example a filling for a drilled-out tooth (1), a crown, bridge or prosthesis to be placed on a tooth stub, or a tooth pin to be fixed in a tooth root for fastening an artificial tooth, a bridge or a prosthesis. The preparation has surface regions which consist of a material with thermoplastic properties. The preparation (10, 11, 12,13) is designed in a manner such that it has oscillation properties with such low damping losses that for a lique-faction of the material with thermoplastic properties by way of oscillations there are local stress concentrations required, and in a manner such that such stress concentrations only occur in the region of the preparation surface. The preparation is positioned on a suitably prepared natural tooth part in a manner such that the material with the thermoplastic properties is in contact or may be brought into contact with the dentin surface and/or enamel surface. The preparation is then made to mechanically oscillate and is simultaneously pressed against the natural tooth part, whereby the material with the thermoplastic properties is at least partly liquefied and brought into intimate contact with the dentin or enamel surface in a manner such that after solidification it forms a positive fit and/or material fit connection. Teeth restored with such preparations have a high stability and a long life, which in particular is attributed to the fact that the thermo-plastic material, in contrast to cements used for the same purpose, shrinks less and has the ability to relieve internal stress by creeping.

20 Claims, 4 Drawing Sheets

U.S. PATENT DOCUMENTS

| | | |
|---|---|---|
| 4,328,108 A | 5/1982 | Deeken |
| 4,360,343 A | 11/1982 | Hussein |
| 4,449,281 A | 5/1984 | Yoshida et al. ........... 29/421 R |
| 4,482,795 A | 11/1984 | Hinden |
| 4,525,147 A | 6/1985 | Pitz et al. |
| 4,566,138 A | 1/1986 | Lewis et al. |
| 4,675,972 A | 6/1987 | Bappert et al. |
| 4,717,302 A | 1/1988 | Adams et al. |
| 4,761,871 A | 8/1988 | O'Connor et al. |
| 5,004,422 A | 4/1991 | Propper |
| 5,019,083 A | 5/1991 | Klapper et al. |
| 5,037,442 A | 8/1991 | Wintermantel et al. |
| 5,097,585 A | 3/1992 | Klemm ........................ 29/523 |
| 5,125,442 A | 6/1992 | Hendrickson |
| 5,163,960 A | 11/1992 | Bonutti |
| 5,167,619 A | 12/1992 | Wuchinich |
| 5,171,148 A | 12/1992 | Wasserman et al. |
| 5,244,933 A | 9/1993 | Eidenbenz et al. |
| 5,271,785 A | 12/1993 | Devine |
| 5,308,205 A | 5/1994 | Lautenschlager |
| 5,393,559 A | 2/1995 | Shoesmith et al. |
| 5,413,578 A | 5/1995 | Zahedi |
| 5,426,341 A | 6/1995 | Bory et al. |
| 5,447,592 A | 9/1995 | Berce et al. |
| 5,547,325 A | 8/1996 | Tucker et al. |
| 5,562,450 A | 10/1996 | Gieloff et al. |
| 5,589,015 A | 12/1996 | Fusco et al. |
| 5,593,425 A | 1/1997 | Bonutti et al. |
| 5,709,823 A | 1/1998 | Hahn |
| 5,735,875 A | 4/1998 | Bonutti et al. |
| 5,752,831 A | 5/1998 | Padros-Fradera |
| 5,766,009 A | 6/1998 | Jeffcoat |
| 5,772,359 A | 6/1998 | Marty |
| 5,780,536 A | 7/1998 | Yokoyama et al. |
| 5,785,476 A | 7/1998 | McDonnell |
| 5,803,736 A | 9/1998 | Merritt, Jr. |
| 5,840,154 A | 11/1998 | Wittmaier |
| 5,871,514 A | 2/1999 | Wiklund et al. |
| 5,871,515 A | 2/1999 | Wiklund et al. |
| 5,897,578 A | 4/1999 | Wiklund et al. |
| 5,919,215 A | 7/1999 | Wiklund et al. |
| 5,941,901 A | 8/1999 | Egan |
| 5,964,764 A | 10/1999 | West, Jr. et al. |
| 5,993,458 A | 11/1999 | Vaitekunas et al. |
| 5,993,477 A | 11/1999 | Vaitekunas et al. |
| 6,007,539 A | 12/1999 | Kirsch et al. |
| 6,039,568 A | 3/2000 | Hinds |
| 6,056,751 A | 5/2000 | Fenton, Jr. |
| 6,059,817 A | 5/2000 | Bonutti et al. |
| 6,068,482 A | 5/2000 | Snow |
| 6,080,161 A | 6/2000 | Eaves, III et al. |
| 6,099,313 A | 8/2000 | Dorken et al. |
| 6,132,214 A | 10/2000 | Suhonen et al. |
| 6,139,320 A | 10/2000 | Hahn |
| 6,141,874 A | 11/2000 | Olsen |
| 6,193,516 B1 | 2/2001 | Story |
| 6,224,373 B1 | 5/2001 | Lee et al. |
| 6,273,717 B1 | 8/2001 | Hahn et al. |
| 6,332,885 B1 | 12/2001 | Martella |
| 6,545,390 B1 | 4/2003 | Hahn et al. |
| 6,592,609 B1 | 7/2003 | Bonutti |
| 6,635,073 B2 | 10/2003 | Bonutti |
| 2001/0045289 A1 | 11/2001 | Cook et al. ................. 166/380 |
| 2002/0044753 A1 | 4/2002 | Nagayama et al. |
| 2002/0077662 A1 | 6/2002 | Bonutti et al. |
| 2003/0118518 A1 | 6/2003 | Hahn et al. |

FOREIGN PATENT DOCUMENTS

| | | |
|---|---|---|
| DE | 257797 | 2/1987 |
| DE | 3723643 A1 | 7/1987 |
| DE | 3828340 | 8/1988 |
| DE | 3919274 C1 | 6/1989 |
| DE | 9012044.2 | 8/1990 |
| DE | 9012548.7 | 9/1990 |
| DE | 4100636 A1 | 1/1991 |
| DE | 4209191 A1 | 3/1992 |
| DE | 4328108 | 8/1993 |
| DE | 0317757.7 | 11/1993 |
| DE | 19735103 A1 | 8/1997 |
| DE | 19741087 | 9/1997 |
| DE | 19916158 A1 | 4/1999 |
| DE | 19916160 A1 | 4/1999 |
| DE | 20113692 U1 | 8/2001 |
| EP | 0268957 | 6/1988 |
| EP | 0415615 | 8/1990 |
| EP | 0451932 A1 | 4/1991 |
| EP | 0534078 A1 | 7/1992 |
| EP | 0617935 | 10/1994 |
| EP | 1044655 | 3/2000 |
| EP | 1044656 A1 | 10/2000 |
| EP | 1184006 | 3/2002 |
| EP | 1199049 | 4/2002 |
| FR | 1164445 | 1/1957 |
| FR | 1407582 | 9/1964 |
| FR | 1495999 | 10/1966 |
| FR | 2205402 | 11/1973 |
| FR | 2455502 | 5/1979 |
| FR | 2615786 | 5/1987 |
| FR | 0269476 | 10/1987 |
| GB | 762906 | 12/1956 |
| GB | 1203305 | 8/1970 |
| GB | 2061183 | 5/1981 |
| GB | 2277448 | 11/1994 |
| GB | 2324470 | 10/1998 |
| JP | 55121024 | 9/1980 |
| JP | 56139918 | 10/1981 |
| JP | 61104817 | 5/1986 |
| JP | 05245941 | 9/1993 |
| JP | 07222752 | 8/1995 |
| JP | 07300904 | 11/1995 |
| JP | 10323351 A1 | 12/1998 |
| WO | WO 88/03391 | 5/1988 |
| WO | WO 91/03211 | 3/1991 |
| WO | WO 94/18373 | 8/1994 |
| WO | WO 96/01377 | 1/1996 |
| WO | WO 96/37163 | 11/1996 |
| WO | WO 98/42988 | 10/1998 |
| WO | WO 01/09445 | 2/2001 |
| WO | WO 02/069817 | 3/2002 |
| WO | WO 02/38070 A1 | 5/2002 |
| WO | WO 02/087459 | 11/2002 |

OTHER PUBLICATIONS

The Simon and Schuster Complete Guide to Home Repair and Maintenance (p. 45).

"Linear Vibration Welding of Non Metallic Components", Welding & Metal Fabrication, May 1989, pp. 152–154.

PREPARATION FOR BEING FASTENED ON A NATURAL TOOTH PART OR TOOTH AND CORRESPONDING FASTENING METHOD

BACKGROUND OF THE INVENTION

Field of the Invention

The invention is in the field of dental medicine and relates to a preparation suitable for being fastened on a natural tooth part or tooth; in particular it is suitable as an artificial replacement of a load-bearing tooth part. The invention further relates to a method for fastening the preparation on a natural tooth part or tooth, in particular the replacement of a load-bearing tooth part (e.g. endodontic restoration), wherein the preparation according to the invention is fastened on a still existing natural tooth part, or is anchored thereto.

Tooth restorations which proceed from a tooth which is still at least partly present, i.e. from a natural tooth part and in which another natural tooth part is replaced by an artificial tooth part, are e.g. the filling of drilled-out teeth, the insertion of inlays, the placing of crowns, bridges or part-prostheses on natural tooth stumps, the fixing of root pins or similar means for fastening e.g. artificial teeth, bridges or tooth prostheses in natural tooth roots or parts thereof. On the other hand, it is also known to fasten veneers, jewellery elements or fixation elements for tooth correction wires on complete natural teeth.

For filling drilled-out natural teeth, for placing crowns on natural tooth stumps and for fastening root pins in a natural tooth root according to the state of the art, parts of metals, polymers, ceramic materials or composite materials (filling body, crown, root pin) are fastened on or in the natural tooth part with the help of polymeric cements. The cements are applied in a viscous condition and are then cured in situ, for example, with ultraviolet light. After complete curing, these cements can meet (in the same way as the parts being fastened by the cements) the demands of the high loading to which teeth are subjected.

The curing of the cements, however, often entails shrinkage. Such shrinkage often causes cracks between the natural and artificial tooth parts into which moisture and bacteria penetrate. Furthermore, the cement may swell up due to moisture, thereby damaging the tooth irreversibly. The bacteria cause decay on the natural tooth part. Furthermore, the cured cements are usually very brittle and, as a result, stress caused by shrinkage and/or swelling cannot be reduced, or can be reduced only by crack formation. Due to the above mentioned phenomena, tooth fillings fixed with the aid of polymeric cements are less toxic than amalgam fillings, but do not last as long.

In order to render the cement shrinkage as small as possible, the cements are applied already partly cross-linked. This solution of the shrinkage problem, however, has very great limitations since the more cross-linked the cement is on application, the more viscous the cement is and, thus, the more difficult it is to securely place the cement so that it completely fills the cavities to be filled.

In U.S. Pat. No. 5,244,933, it is suggested to use in the dental field, polymeric cements that contain a high share of inorganic particles for improving the mechanical properties of the polymeric cements in the cured condition. These cements are highly viscous, and therefore, it is suggested to bring them into an improved flowing condition in situ by applying high frequency vibrations. This effect is based on the thixotropic properties of such cements and the corresponding liquefaction does not entail heat development. However, the problem of shrinkage is not solved at all.

Shrinkage cannot be tolerated, for example, in the case of tooth canal sealing. For this reason, the above-mentioned cements are not used for this purpose, but instead, for example, gutta-percha or other thermoplastic polymers with similar properties as gutta-percha are used. When being applied in the root canal, the polymer is brought to a plastic condition by warming and then can be re-solidified by cooling. In such a case, the shrinkage is significantly smaller than the shrinkage due to curing by cross-linking. Such methods for sealing root canals are, for example, described in U.S. Pat. Nos. 3,919,775 and 4,525,147. According to these patents, a gutta-percha plug is introduced into the root canal. It is then, in its entirety, brought into a plastic condition by heat and/or ultrasound and is pressed into the canal. This is possible without unreasonable thermal loading only if the material has a low softening temperature (gutta-percha: 70 to 100° C.). The softening temperature thus limits the material choice. The function of the gutta-percha plug is the sealing of the root canal. The plug is not mechanically loaded at all. Indeed, it would not be capable of being mechanically loaded due to the limited mechanical strength of the material, even if it were to contain carbon fibers, as suggested in U.S. Pat. No. 4,525,147.

The disclosure of U.S. Pat. No. 5,803,736 also describes production of casts for root canals, in which production shrinkage cannot be tolerated either. It is suggested to use thermoplastic polymers, which are applied in a heated and, thus, plastic condition. For preventing heat damage to the natural tooth part, the polymers to be used are limited to those with a softening temperature of 50 to 70° C. Polycaprolactone is suggested as being particularly advantageous as it has a softening temperature of 55 to 65° C. and a modulus of elasticity of approx. 400 MPa. It is clear that such a polymer cannot be applied for a load-bearing function in the dental field.

Many known root pins have a round cross section and a straight axis and are placed in a corresponding bore with a round cross section and a straight axis that is formed in the tooth root. Since the tooth root does not have a round cross section or a straight axis, the bore and the pin may only have very limited dimensions. Nonetheless, as the case may be, a significant part of the root must be removed by producing the bore. This sets narrow limits on the stability of the fixed root pin.

SUMMARY OF THE INVENTION

The objects of the invention are to create a preparation for being fastened on a natural tooth part or tooth, in particular for replacing a load-bearing tooth part, and to create a method for fastening the preparation on the natural tooth part or tooth, in particular in order to replace a load-bearing tooth part by the preparation according to the invention. The preparation and the method are to make it possible to avoid the above-outlined shrinkage problems and the life span limitations due to shrinkage of the fastening or the tooth restoration respectively. In spite of this, neither the preparation nor the method are to be more complicated than corresponding artificial tooth parts and fastening methods according to the state of the art.

The invention is based on the knowledge that it is possible to create positive-fit and/or material-fit connections between the surfaces of a natural tooth part or tooth (dentin and/or enamel) and a material with thermoplastic properties in a liquid or at least plastic condition, which connections are able to meet the mechanical, chemical and biological demands in the dental field. It is further based on the knowledge that there are known materials with thermoplastic properties that are able to fulfil the strength requirements of a load-bearing tooth part, and that it is possible to create the mentioned connections with such materials without unreasonable thermal loading of the tooth part to be restored if only a minimal of the material with thermoplastic properties necessary for creating the connections is liquefied.

For creating the mentioned positive-fit and/or material-fit connections, a process is used that is derived from the process of welding by mechanical oscillation (e.g. ultrasound welding). These welding processes are based essentially on oscillating a body of a thermoplast or a body with surface regions of a thermoplast with a frequency in the ultrasound range and with amplitudes on the order of 1 to 200 $\mu$m, and at the same time bringing the body in a pointwise manner or in small surface regions (energy directors) into direct contact with another surface. In the contact regions, stress concentrations arise in the oscillating material and due to these stress concentrations, the material (even if it has a relatively high softening temperature) is brought into a plastic or liquid condition so that a weld connection is achieved, provided there is suitable material pairing (e.g. two mixable thermoplasts).

The preparation according to the invention comprises at least partly of a material with thermoplastic properties and it is designed in a manner such that it damps mechanical oscillations very little so that the material is liquefied by way of mechanical oscillation only at locations where stress concentrations arise, as is the case with ultrasound welding. The locations of the stress concentrations are produced by energy directors likewise known from ultrasound welding technology, which are to be provided or present on outer surfaces (also inner surfaces as the case may be) of the preparation, or on surfaces of the natural tooth part in contact with the preparation.

The further surface to which the material with thermoplastic properties is to be connected is a surface of a natural tooth part and consists of dentin and/or enamel which are both in no way suitable for a weld connection. These surfaces however have structures (macroscopic, microscopic and/or molecular), or are provided with such structures, with which the material liquefied by the mechanical oscillation comes into such intensive contact that after solidification is forms a positive-fit and/or material fit connection with these structures.

The materials or material systems which may be used in the preparation according to the invention must have sound-conducting properties and a sufficiently low damping so that the preparation is capable of oscillating. Typically this necessitates a modulus of elasticity of at least about 0.5 GPa. The loss factor should be sufficiently high for liquefaction in the regions of stress concentrations. It has been shown that for the tooth restoration according to the invention, thermoplastic materials with softening temperatures of up to approx. 350° C. are applicable, wherein the mechanical oscillations are to be applied for approx. 0.1 to 10 sec. Heat quantity and exposure time remain so small that thermal damage of the dentin or the surrounding vital tissue is not to be expected.

The mentioned conditions with respect to modulus of elasticity and softening temperature are fulfilled by many materials with thermoplastic properties (thermoplasts or composite material with a thermoplastic component, hereinafter called thermoplastic materials) which materials can not only fulfill the mechanical requirements of a load-bearing or load-transmitting tooth part, but are already used in other medical applications.

At least a part of the surface of the preparation according to the invention consists of the thermoplastic material, wherein on restoration, this surface region is in contact or is able to be brought into contact with a surface of the tooth part to be restored or with a tooth. Furthermore, the preparation according to the invention may comprise areas suitable as energy directors in the surface regions of the thermoplastic material, that is to say edges, tips, integrally formed parts or areas of roughness that project at least 0.5 $\mu$m beyond the rest of the surface. The function of the energy directors may, however, also be assumed by a suitable shaping of the tooth part to be restored or of another part of the preparation.

The regions of the preparation surface through which the oscillations are coupled to the preparation are advantageously to be designed such that no stress concentration arises there.

For restoration, the preparation is positioned on the natural tooth part or tooth to be restored or in this tooth part and is then made to oscillate by suitable means, for example by the sonotrode of an ultrasound apparatus, and at the same time it is pressed against the natural tooth part or tooth. Suitable frequencies lie between 2 and 200 kHz (in particular 20 to 80 kHz), suitable oscillation amplitudes between 1 and 200 $\mu$m. Experiments have shown that good results are achieved with an oscillation power of 2 to 20 W per square millimeter of active surface. The thermoplastic material is locally (in particular on its surface in contact with the natural tooth part or close to this surface) liquefied by the oscillations transmitted to the preparation and is brought into intimate contact with the surface of the natural tooth part or tooth, by way of which the positive-fit and/or material-fit connection is produced. The optimal matching of amplitude and power to a specific type of preparation according to the invention is to be determined experimentally. Advantageously, amplitude, power and preparation are to be matched to one another in a manner such that there is an optimal transmission of the sound power to the surface of the preparation.

The connections between the surface of the natural tooth part and the thermoplastic material which are created according to the invention are in particular positive-fit connections produced by pressing the liquefied material into pores and surface unevenness of the natural tooth part. There may, however, also be material-fit connections which are caused by adhesive exchange forces. In all events, in order to create the connections, intimate wetting of the natural surfaces with the liquefied, thermoplastic material is required.

For improving such wetting or for improving the connections to be created, respectively, the concerned natural surfaces may be suitably prepared. For example an enamel surface or a dentin surface may be roughened for achieving a positive fit (advantageous roughness: 0.5 to 500 $\mu$m). For achieving improved positive-fit connections, one may also create retention structures on the surfaces of the dentin or enamel, such as thread convolutions, furrows, recesses with depths of 0.1 to 2 mm and possibly undercuts. Before positioning the preparation according to the invention, the natural surfaces may be pre-treated or etched with a suitable primer for improving wettability of the natural surfaces by the thermoplastic material and/or for achieving increased adhesive exchange forces. Applicable primer systems comprise, in a per se known manner, chemical reactive compounds reacting with the natural tooth material and/or molecular functionalites cooperating with corresponding functionalites on the side of the thermoplastic material. Such cooperating functionalities are, for example, matching of polarities of the two sides for increasing exchange forces, interpenetrating oligomers or reactive components which bind the two sides chemically when activated by the oscillations, by light, by heat or by chemical activation.

Suitable thermoplastic materials for the preparations according to the invention are, for example polyolefins, polyacrylates, polymethacrylates, polyurethanes, polycarbonates, polyamides, polyesters, polyurethanes, polysulphones, polyaryl ketones, polyimides, polyphenyl sulphides, liquid crystal polymers (LCPs), polyacetals, halogenated polymers, in particular halogenated polyoelefins, polyphenylene sulphides, polysulphones or polyethers. Corresponding copolymers or polymer mixtures are applicable also. The mentioned thermoplasts may also be applied in a filled condition (composite material with a thermoplastic component), i.e. contain fibres, whiskers or particles of glass, ceramic materials, carbon or polymers, wherein the filling may be homogeneous or have gradients.

The material with thermoplastic properties may in, a per se known manner, be equipped with agents acting antiseptically or in a denaturising manner, or with x-ray absorbing additions, or it may contain pigments known in dental medicine.

The preparation according to the invention, for example, may have the shape of a tooth part (tooth filling) to be positioned into a drilled-out tooth, or the shape of a crown, a bridge, a full or partial prosthesis, or a root pin to be inserted into a natural tooth root being possibly pre-machined, wherein the root pin serves to fasten an artificial tooth, bridge or prosthesis. The preparation according to the invention may also have the shape of an element to be placed onto a tooth (e.g. veneer, capping, jewellery piece, fixation means). The preparation according to the invention may be a unitary piece consisting of the thermoplastic material only, or the preparation according to the invention may comprise at least surface regions of the thermoplastic material and further regions consisting of another material that satisfies the demands regarding mechanical strength and oscillation capability. Metallic or ceramic materials, polymers, or composite materials already used in dental medicine are applicable for this purpose.

A preparation according to the invention that consists of two different materials, one of which has thermoplastic properties and one of which may consist of ceramic or metal, may comprise two or more parts, wherein a preparation part consisting of the thermoplastic material is positioned between the natural tooth part or tooth.

The main advantages of the preparation and method of the invention with respect to the above mentioned, known tooth restoration methods are: the significantly reduced shrinkage of the material that must be plastified or liquefied on restoration, the inherent ability of this material to creep and thereby relieve inner stress without crack formation, and the inherent insensitivity of this material to moisture. These three properties lead to a high stability and a high life expectancy of the restored teeth. The method according to the invention in comparison to the above mentioned known method has less method steps (no curing step), requires less time and is more economical. A further advantage of the restorations according to the invention lies in the fact that cooling, which is the only necessary step for solidifying the thermoplastic material, is reversible. This means that it should be possible to repeat the application of the mechanical oscillation in order to deal, for example, with cracks between natural and artificial tooth parts or within the artificial tooth part and thereby reverse the restoration in a very simple manner.

BRIEF DESCRIPTION OF THE DRAWINGS

The method according to the invention and exemplary embodiments of the preparation according to the invention are described in detail in combination with the following Figures. The observations described in the preceding sections and further features of the preparation according to the invention are accordingly applicable to all embodiment forms.

DETAILED DESCRIPTION OF THE PREFERRED EMBODIMENTS

Figure 1:
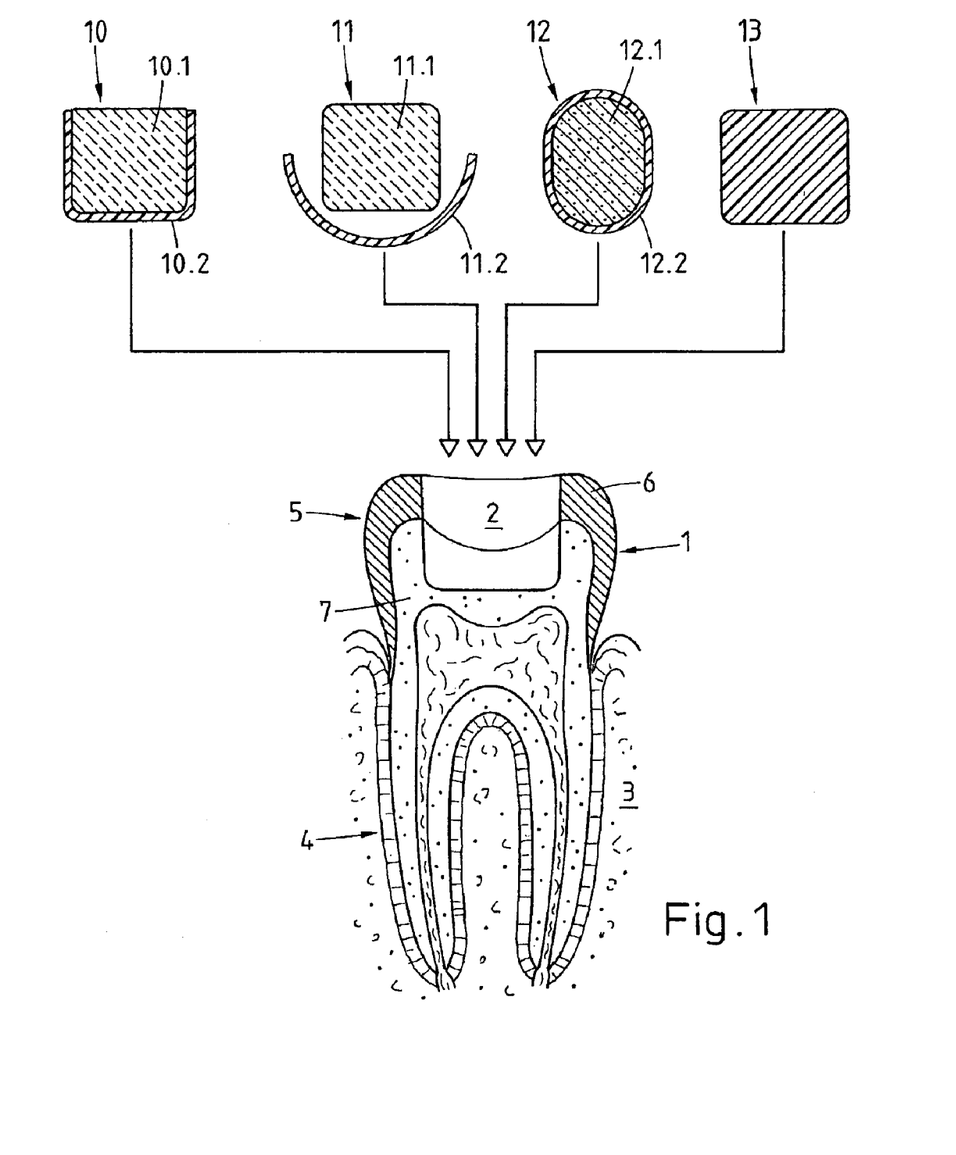
FIG. 1 shows four exemplary embodiments of preparations according to the invention, used for filling a drilled-out tooth (longitudinal section)

FIG. 1 shows a plurality of ways a tooth cavity may be filled according to the invention. In FIG. 1, a tooth 1 is shown drilled out, for example, because of caries and therefore, having an opening 2 to be filled. The tooth 1 is shown sectioned along its longitudinal axis. It comprises a root 4 grown into the bone tissue 3 of the jaw and a crown 5 projecting beyond the jawbone and being coated with enamel 6. The supporting element of the tooth is the dentin 7, consisting of porous dentin. Inside the dentin 7 there is a tooth cavity filled with connective issue (pulp) comprising vasculature and nerves. The opening 2 extends through the enamel 6 into the dentin 7, i.e. it has an accessible surface within the opening 2 which opening has an open-pore structure. Additionally, the dentin surface as well as the enamel surface in the opening may be pre-treated (e.g. by roughening, structuring, etching or primer treatment) for improving the connection between the natural tooth part and the preparation to be applied.

According to the invention, in order to restore the drilled-out tooth 1 shown in FIG. 1, the opening 2 may be filled with one of the preparations 10, 11, 12, 13 shown above the drilled-out tooth 1.

Preparation 10 comprises a body 10.1 of a known filling body material and a contact layer 10.2 consisting of thermoplastic material and completely or partly covering the surface of the body 10.1. For example, the one side of the preparation to be facing toward the outside when the preparation is positioned in the opening 2 is free of thermoplastic material. The preparation 10 is dimensioned in a manner such that it can be positioned at least partly in the opening 2 essentially without using force.

The preparation 10 is positioned in the opening 2 and is then excited with mechanical oscillation using a resonator (not shown) of a device producing mechanical oscillation (such as a sonotrode of an ultrasound apparatus) and the preparation is simultaneously pressed into the opening 2. As a result, the material of the contact layer 10.2 is at least partly liquefied and through the applied pressure is brought into intimate contact with the enamel 6 and dentin 7, which leads to a positive-fit and adhesive connection. As the case may be, the preparation is simultaneously pushed further into the opening 2. The oscillation excitation is stopped when the preparation body 10.1 has been pushed sufficiently into the opening and no more thermoplastic material can be pressed into pores and unevennesses, as evidenced by material being pressed out between the enamel and the body 10.1. At the same time the pressing pressure is advantageously maintained until the thermoplastic material has resolidified. After solidification of the thermoplastic material, the body 10.1 may be adapted to the shape of the original tooth using known dental technology. At the same time, if so required, the contact layer 10.2 may be removed from the top of the preparation body 10.1.

The preparation 11, which is likewise suitable for filling the tooth opening 1, differs from the preparation 10 only in that in place of a contact layer fastened to the body it comprises a separate contact film 11.2, which may be applied separately from the body 11.1 and which consists of the material with thermoplastic properties. The contact film 11.2 is brought into the opening before positioning the body 11.1 or simultaneously therewith.

The preparation 12 comprises a preparation body 12.1 of highly viscous composite material as known in dental medicine (for example, cement curable by light, heat or ultrasound, or ormocer-like system). The preparation body 12.1 is enclosed in a preferably flexible contact layer 12.2 of the thermoplastic material. The material of the preparation body 12.1 and the contact layer 12.2 are matched to one another in a manner such that a connection arises between them (e.g. by silanisation, surface-activation, graft-polymerisation of reactive groups on the side of the contact layer).

The advantage of the preparation 12 with respect to the preparations 10 and 11 lies in the fact that it may be adapted to the shape of the opening 2 to a greater extent than the previously described preparations. The disadvantage of shrinkage entailed by the composite material is made up by the connection between the cured composite material and the thermoplastic material, which leads to the fact that stress caused by shrinkage of the cement may be transmitted to the thermoplastic material and may be relieved by relaxation or creeping.

The contact layer 12.2 may also be relatively stiff and open to the top, such that the dentist can fill it with the cement. In this case, it is advantageous to cover the cement with a cover element (e.g. Teflon film, metal film, metal element, etc.) for applying the oscillations.

The contact layers 10.2 or 12.2 or the contact film 11.2 advantageously have a thickness of approx. 0.01 to 1 mm. It is in no way necessary for the contact layer or film to have the same thickness at all locations and to cover all surfaces of the preparation coming into contact with the natural tooth part. Advantageously, it comprises, on the one surface facing the dentin, energy directors in the form of ribs, pyramids, cones, hemispheres, etc. that project by at least 1 $\mu$m. The function of the energy directors may also be assumed by the dentin/enamel surface. In the case of a preparation 11 comprising a contact film 11.2, it is also possible to equip the surface of the preparation body 11.1 with energy directors.

The thermoplastic material of the contact layers 10.2 or 12.2 or the contact film 11.2, as already mentioned above, may contain reactive resins that react with the natural tooth material or with a primer deposited thereon to form chemical bonds.

The preparation 13, which is likewise suitable for filling the opening 2, does not comprise a preparation body composed of non-thermoplastic material surrounded by a contact layer or film. Rather, the preparation 13 consists entirely of a thermoplastic material, advantageously of a filled thermoplast, wherein the extent of filling may increase from the periphery of the preparation towards its centre. The thermoplastic material may additionally contain pigments known in the art of tooth fillings. The preparation 13 is adaptable to the shape of the opening 2 to a better extent than the preparations 10 and 11 since the available quantity of thermoplastic material is larger.

The cavity 2, as described above, may be filled with one of the preparations 10 to 13. It may also be filled with a plurality of equal or different preparations, wherein a first preparation is positioned and mechanical oscillation applied to it. Then a second preparation is positioned and mechanical oscillation is applied to it, and so forth.

Figure 2:
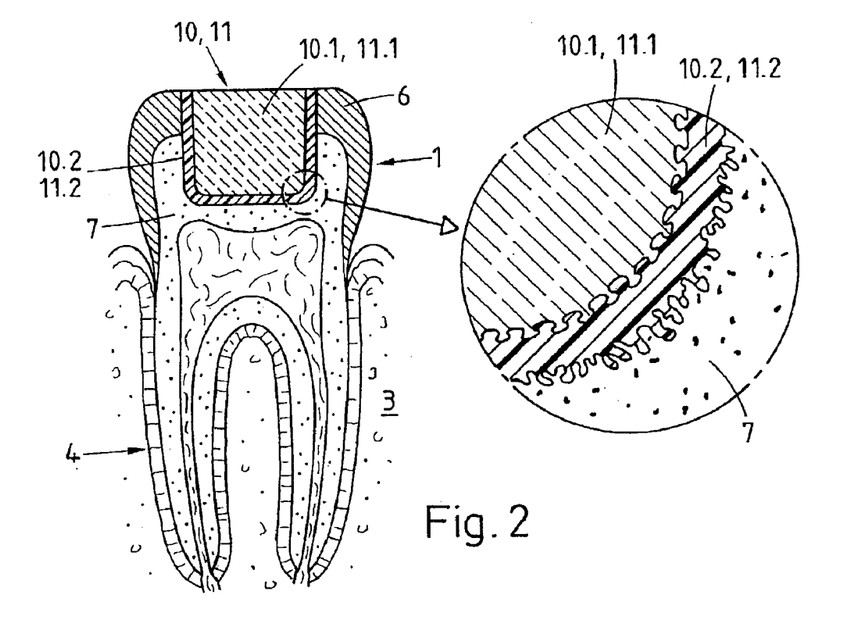
FIG. 2 shows a tooth filled with a preparation according to FIG. 1 (longitudinal section)

If the opening is not only accessible from the end face as shown in FIG. 2, but also from the side, it is advantageous to use an auxiliary device known in the state of the art e.g. sleeve) when applying the preparations 10 to 13 and to remove it afterwards. This auxiliary device has an inner surface on which the thermoplastic material is not liquefied or from which it is easily separated. On the open side, the contact layer or film is removed when the preparation is positioned and fixed.

FIG. 2 shows the same tooth as FIG. 1 but with the opening 2 filled with the preparation 10 or 11 and after adaptation of the outer surface to the original shape of the tooth. FIG. 2 further shows, in a larger scale, the contact layer 10.2 or contact film 11.2 being connected to the dentin, i.e. after liquefying and pressing the thermoplastic material into the pores of the dentin 7. From this detail, one may recognize the positive fit between the tooth part and the preparation that is produced by liquefying the thermoplastic material and pressing it into pores or surface irregularities of the dentin and, as the case may be, of the enamel. The positive fit ensures a very stable anchoring of the preparation. As may likewise be recognized from the enlarged detail, it is advantageous to design the surface of the preparation body 10.1 or 11.1 in a manner such that here too a positive fit (or also adhesive connection) between the material of the body and the thermoplastic material is possible. For this, the surface of the preparation body 10.1 or 11.1 may be designed suitably rough (roughness of approx. 0.5 to 50 $\mu$m) or may be provided with a suitable surface structure on the sides on which it is surrounded by thermoplastic material. It is also conceivable to manufacture the corresponding surfaces of the preparation body 10.1 or 11.1 of a porous, for example sintered material (pores with sizes of 10 to 300 μm, porosity of 2 to 80%).

Figure 3:
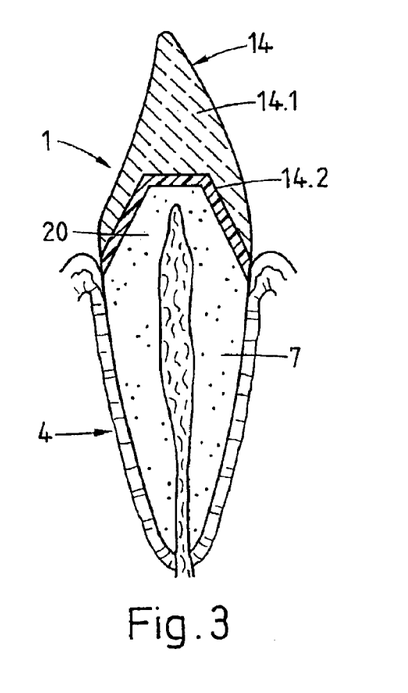
FIG. 3 shows the crowning of a tooth stump with the help of a preparation according to the invention (longitudinal section)

FIG. 3 shows as a further embodiment of the preparation according to the invention, an artificial crown 14 to be placed on a natural tooth stump 20. The crown 14 comprises a crown body 14.1 of a material known for this purpose (e.g. tooth alloys, plastics, composites, ceramic compounds). Between the crown and the dentin 7 there is again located a contact layer 14.1 consisting of a thermoplastic material and being designed as a coating of the crown body 14.1 (analogous to the contact layer 10.1 of preparation 10) or as a separate contact film (analogous to the contact film 11.2 of preparation 11). The contact layer 14.1 is connected to the dentin 7 of the tooth stump by way of mechanical oscillation excitation and pressing, and as the case may be, is also anchored in a corresponding surface structure of the crown body 14.1 in a similar way as shown in FIG. 2. The preparation 14 may not only be a crown, but in the same manner may be a bridge, a prosthesis or a part prosthesis.

Figure 4:
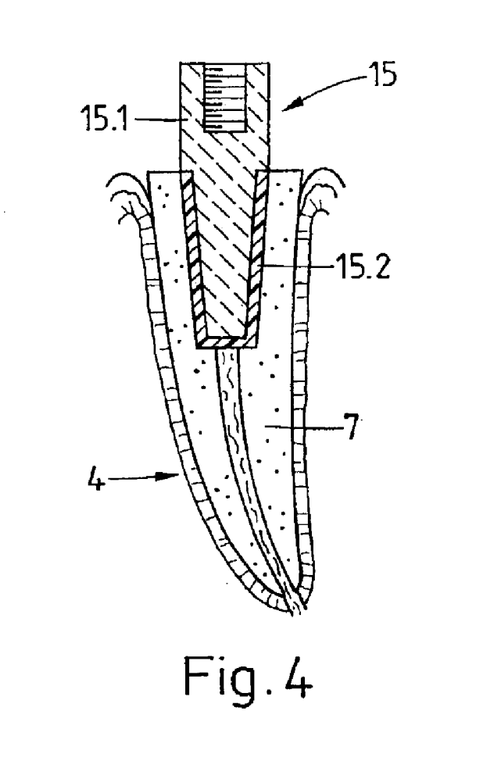
FIG. 4 shows an embodiment of the preparation according to the invention, which preparation has the form of a root pin (longitudinal section) to be fixed in a suitably prepared, natural tooth root.

FIG. 4 shows a further embodiment 15 of the preparation according to the invention, which has the shape and function of a fastener body for a crown, bridge or prosthesis (e.g. root pin) and which is positioned and fixed in a suitably prepared (drilled out) tooth root and to which an artificial tooth, a bridge, a part prosthesis or a full prosthesis is fastened. The preparation comprises a preparation body 15.1 and a contact layer 15.2 or contact film, but may also completely consist of the thermoplastic material. The preparation 15 is designed in the same manner as the tooth fillings 10, 11 or 13 according to FIGS. 1 and 2. Thus, the description of these Figs. may be applied accordingly. At its proximal end, the preparation is provided with fastener means, for example as shown with a pocket hole with an inner thread. Such a fastener means may of course also be created after the preparation has been positioned and fixed in the tooth root.

Figure 5:
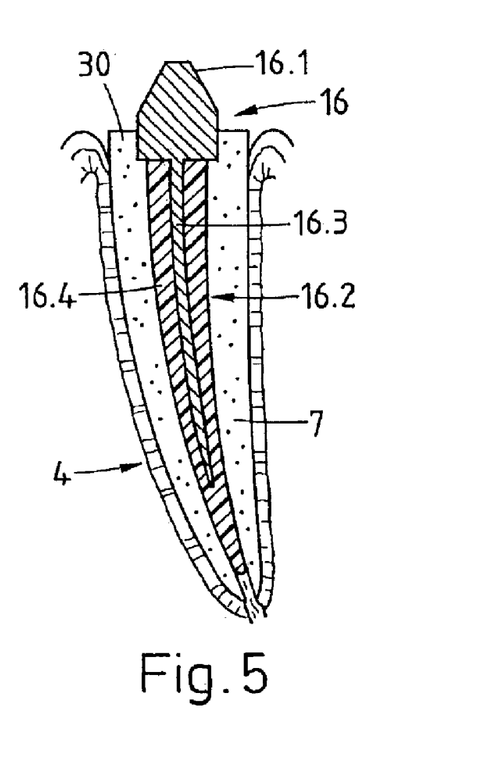
FIG. 5 shows a further, exemplary embodiment of the preparation according to the invention, which preparation serves in the same way as a root pin for fastening an artificial tooth, a bridge or prosthesis on a natural tooth root (longitudinal section)

FIG. 5 shows a further example 16 of a preparation according to the invention. It is also a preparation that serves to fasten an artificial tooth part (root pin) and comprises a fastener body 16.1 The fastener body 16.1 consists of a material suitable for the load-bearing function, such as titanium. A root part 16.2 mounted on the fastener body comprises a core 16.3 (such as titanium wire) being elastically or plastically deformable and therefore adaptable to a specific root canal, and a covering 16.4 of the thermoplastic material enveloping the core 16.3. The root part 16.2 is at least partly positioned in the cavity of the suitably prepared, natural tooth root (e.g. drilled out for accommodating the fastener body) and adapts to the shape of this cavity. The fastener body 16.1 projecting beyond the tooth root 4 is then excited with mechanical oscillation and pressed against the tooth root 4 so that it comes to sit in a seat 30 suitably prepared on the surface of the tooth root 4, and the root part is pushed as deep as possible into the hollow of the tooth root. At the same time, the covering material is at least partly liquefied and adapts to the canal shape and the thermoplastic material is connected to the dentin.

The preparation 16 may also be designed with a plurality of root parts 16.2 for being fixed on a molar root. For this application, it is particularly advantageous for the thermoplastic material of the covering 16.4 to be equipped with antiseptically or denaturising agents.

FIG. 5 shows the preparation 16 in its fixed condition, i.e., after treatment with mechanical oscillations. The fastener body is seated in its seat 30. The core 16.3 of the root part 16.2 is seated in the hollow of the tooth root 4 surrounded by the covering 16.4, whose thermoplastic material is at least partly pressed into the pores and surface unevenness of the dentin 7 and is thus anchored in the natural tooth root. For achieving a good connection between the core 16.3 and the covering 16.4, it may be advantageous to equip the core 16.3 with a suitable surface structure (not shown).

For the preparation according to FIG. 5, it is particularly advantageous to equip the material of the covering 16.4 with antibiotic or antiseptic agents for eliminating the negative effects of pulp remains in the canal. The core 16.3 and the covering 16.4 may both consist of the thermoplastic material, wherein a reinforcing filling in the core region may advantageously have a greater share than in the covering region.

Figure 6:
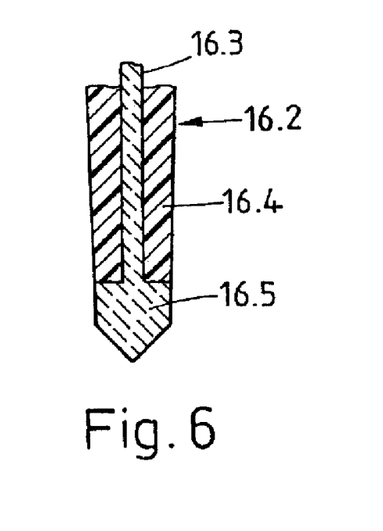
FIGS. 6 and 7 show two exemplary embodiments of the distal ends of a preparation according to FIG. 5.
Figure 7:
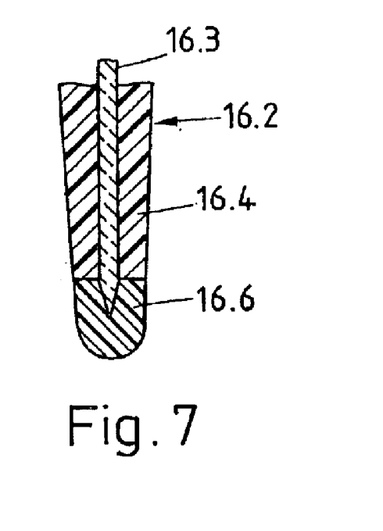

FIGS. 6 and 7 show two variants of the distal end of the preparation 16 according to FIG. 5 that are designed for preventing the root part 16.2 from being able to advance too deeply into the root hollow, and/or for preventing the liquefied material from being able to be pressed out of the root cavity. According to FIG. 6, the core 16.3 comprises a thickening 16.5 which limits the advance in the root canal and/or serves as a seal and which also renders the position of the root part 16.2 clearly visible in an x-ray picture. According to FIG. 7, a plug 16.6 of a soft material, for example of gutta-percha, is arranged at the distal end of the preparation. The plug 16.6, where appropriate, is brought into a plastic condition by way of oscillation of the preparation and may, thus, seal the inner opening of the root canal.

Figure 8:
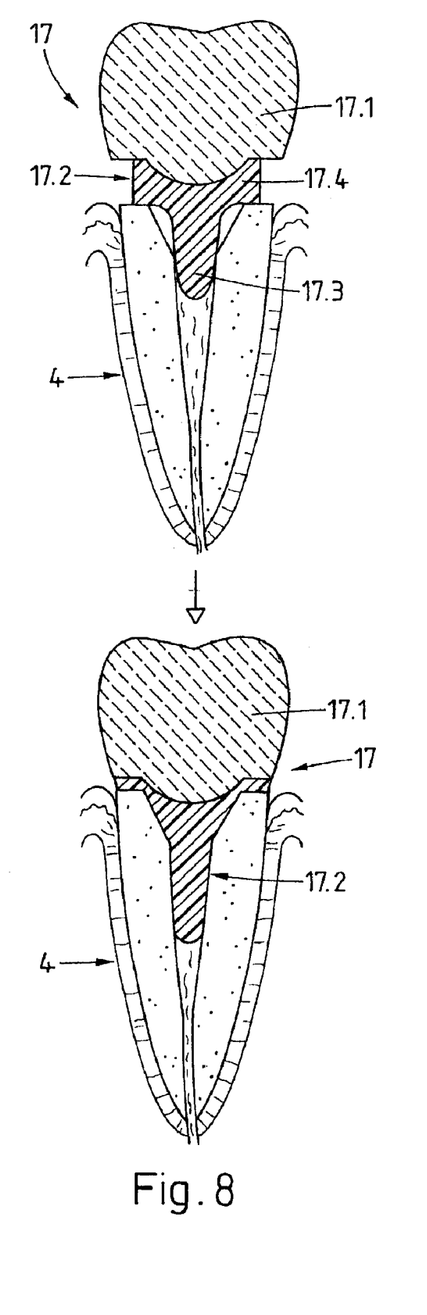
FIG. 8 shows a further exemplary embodiment of the preparation according to the invention in the form of an artificial tooth placed on a natural tooth root (longitudinal section)

FIG. 8 shows a further embodiment 17 of the preparation according to the invention. The preparation has the shape of an artificial tooth to be placed onto a natural tooth root 4. The preparation 17 has a crown part 17.1 and a connection part 17.2, wherein the crown part 17.1 consists of a material suitable for an artificial tooth and the connection part 17.1 consists, at least partly, of the thermoplastic material. The connection part 17.2, which may be fastened on the crown part 17.1 or may be applied independently, is for example formed as a flat plate or a piece of film, or it comprises, as shown, a root appendix 17.3, which at least partly is positionable in the hollow of the tooth root 4 and which is integrally formed on a connection plate 17.4 positionable on the root surface. The connection plate 17.4, for its part, is connected to the crown part 17.1 by a positive fit realized either by the manufacturer or by the dentist on fixing the preparation in the natural tooth root. The preparation 17 of FIG. 8 is shown on the top being positioned on the tooth root 4 (i.e. before the application of the mechanical oscillations) and below in the fixed condition (i.e. after the application of the mechanical oscillations).

When being fixed in a tooth root, the preparation 17 is positioned on the prepared tooth root 4 in a manner such that the root appendix 17.3 is at least partly positioned in the root cavity. Oscillation is then applied to the preparation. In the case of a two-part preparation, both parts are first positioned and then the entire preparation is made to oscillate, wherein the thermoplastic material of the connection body 17.2 liquefies locally, in particular at its contact locations with the dentin. Simultaneously, the preparation is pushed further into the hollow 4 of the tooth root 4. If so designed, the thermoplastic material of the connection body 17.2 is liquefied also at its contact surface with the crown part 17.1 and is pressed into suitably provided surface structures, as this has been described in combination with FIG. 2. It is also possible to first position the connection body 17.2, then connect it to the tooth root by application of oscillations and then position and subsequently connect the crown part 17.1 to the connection body 17.2, once again using oscillations.

In a manner analogous to the one shown and described in FIG. 8, one may not only fix a crown part to a natural tooth root, but also fix another artificial tooth part onto a cavity, specially created for this purpose, in a natural tooth part.

Figure 9:
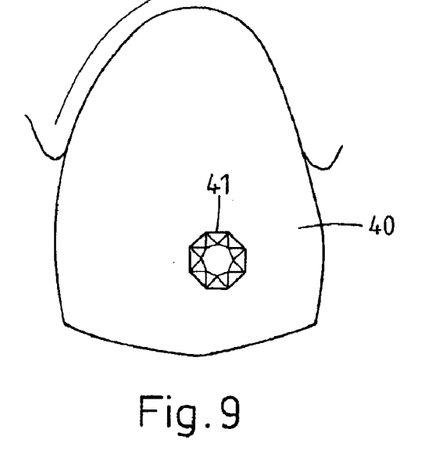
FIG. 9 shows a further exemplary embodiment of the preparation according to the invention in the form of a jewellery element to be placed on a tooth.

FIG. 9 shows a complete natural tooth on which a jewellery element, for example a cut diamond is fastened, wherein the rear side of the jewellery element within the context of the invention carries a layer of material with thermoplastic properties or a suitable film is positioned between the tooth and the jewellery element for the fastening. In the same manner, other elements such as veneers, cappings and fixation elements may be fastened to teeth, for example fixation elements for wires as used for tooth corrections.

What is claimed is:

1. A preparation (10, 11, 12, 13, 14, 15, 16, 17) to be fixed on a natural tooth part or tooth, in particular for replacement of a load-bearing tooth part, said preparation being positionable in the natural tooth part or on the natural tooth part or tooth and comprising:
   at least one region (10.2, 12.2, 14.2, 15.2, 16.2, 17.2) or one part (11.2) of a material with thermoplastic properties, the at least one region forming at least part of the preparation surface and the at least one part being positionable to form at least part of the preparation surface,
   wherein the preparation has oscillation properties with damping losses which are so small that local stress concentrations are required for liquefying the material by oscillation, and
   wherein the preparation is designed in a manner such that the stress concentrations only occur in the region of the preparation surface.

2. The preparation (10, 11, 12, 13, 14, 15, 16, 17) according to claim 1, wherein the material with thermoplastic properties has a modulus of elasticity which is larger than 0.5 Gpa.

3. The preparation,(10, 11, 12, 13, 14, 15, 16, 17) according to claim 2, wherein the material with thermoplastic properties is a thermoplastic material or a composite material with a thermoplastic component.

4. The preparation (10, 11, 12, 13, 14, 15, 16, 17) according to claim 3, wherein the thermoplastic material or the thermoplastic component is a polyolefin, a polyacrylate, a polymetacrylate, a polyurethane, a polycarbonate, a polyamide, a polyester, a polysulphone, a polyarylketone, a polyimide, a polyphenyl sulphide, a liquid crystal polymer, a polyacetal, a halogenated polymer, in particular a halogenated polyolefin, a polyphenylene sulphide, a polysulphone, a polyether or a corresponding copolymer or mixture of at least two of said polymers.

5. The preparation according to claim 1, wherein the material with thermoplastic properties is a thermoplast with admixtures of fibres, whiskers, particles, agents acting antiseptically or in a denaturising manner, or x-ray absorbing constituents.

6. The preparation according to claim 1, wherein the material with thermoplastic properties comprises an active component reacting with the surface of the natural tooth part or with a primer deposited thereon.

7. The preparation (10, 11, 12, 13, 14, 15, 16, 17) according to claim 1, wherein the preparation further comprises a further region (10.1, 12.1, 14.1, 15.1, 16.1, 17.1) or part (11.1) of a metallic or ceramic material, of a polymer or of a composite material.

8. The preparation (10, 11, 12, 13, 41) according to claim 1, wherein the preparation has the shape of a tooth filling to be fixed in a tooth opening (2), or the shape of an element (41) to be fixed to a tooth (40).

9. The preparation (10, 11, 12) according to claim 7, wherein the preparation further comprises a preparation body (10.1, 11.1, 12.1) and a contact layer (10.2, 12.2) arranged on the preparation body (10.1, 11.1, 12.1), or a contact film (11.2) forming a separate preparation part.

10. The preparation (13) according to claim 7, wherein the preparation consists entirely of the material with thermoplastic properties.

11. The preparation (14) according to claim 1, wherein the preparation has the shape of a crown, bridge or,prosthesis to be fixed on a natural tooth stump (20), and the material with the thermoplastic properties forms an inner surface of the crown, bridge or prosthesis or is positionable on this inner surface.

12. The preparation (15, 16) according to claim 1, wherein the preparation further comprises a fastener body (15.1, 16.1) to be fixed in a cavity of a natural tooth part, the fastener body being equipped for the fastening a further, artificial tooth part to the fastener body.

13. The preparation (16) according to claim 12, wherein the preparation further comprises at least one root part (16.2) arranged on the fastener body (16.1), the root part comprising an elastically or plastically deformable core (16.3), and a covering (16.4) of the material with thermoplastic properties arranged around the core (16.3).

14. The preparation (16) according to claim 13, wherein at a distal end of the core (16.3) there is arranged a thickening (16.5) of the core material or a plug (16.6) of a soft thermoplast.

15. The preparation (17) according to claim 1, wherein the preparation further comprises a crown part (17.1) and a connection body (17.2), and wherein the connection body (17.2) consists at least partly of the material with thermoplastic properties and is designed in a manner such that it is positionable at least partly in a cavity of a natural tooth part.

16. A method for fastening a preparation (10, 11, 12, 13, 14, 15, 16, 17) comprising at least one region (10.2, 12.2, 14.2, 15.2, 16.2, 17.2) or one part (11.2) of a material with thermoplastic properties, the at least one region forming at least part of the preparation surface and the at least one part being positionable to form at least part of the preparation surface, and the preparation having oscillation properties with damping losses so small as to require local stress concentrations for liquefying the material by oscillation, and the preparation being designed in a manner such that the stress concentrations only occur in the region of the preparation surface, the method comprising the steps of:
   preparing a natural tooth part or tooth,
   positioning the preparation (10, 11, 12, 13, 14, 15, 16, 17) in the region of the prepared tooth part or tooth in a manner such that the material with thermoplastic properties is in contact or can be brought into contact with a dentin surface and/or an enamel surface of the natural tooth part or tooth, and
   exiting the preparation into mechanical oscillation and simultaneously pressing it against the tooth part or tooth.

17. The method according to claim 16, wherein for exciting with mechanical oscillation and for pressing, the preparation is pressed against the natural tooth part or tooth with the aid of a sonotrode of an ultrasound apparatus.

18. The method according to claim 16, wherein in the step of exciting and pressing mechanical oscillations are used with a frequency in the region between 2 and 200 kHz.

19. The method according to claim 16, wherein in the step of preparing dentin and/or enamel surfaces are roughened, provided with retention structures and/or pre-treated with a primer.

20. The method according to claim 16, wherein a two-part preparation (11) is used and wherein in the step of positioning firstly a first preparation part (11.2) comprising the material with the thermoplastic properties is positioned and made to oscillate, and then a second preparation part (12.1) is positioned and made to oscillate.

* * * * *